US00PP11663P

United States Patent [19]

Tokairin

[11] Patent Number: Plant 11,663

[45] Date of Patent: Dec. 5, 2000

[54] PETUNIA PLANT NAMED 'MAGIC STAR'

[75] Inventor: Tomio Tokairin, Aalsmeer, Netherlands

[73] Assignee: Japan Tobacco, Inc., Tokyo, Japan

[21] Appl. No.: 09/144,328

[22] Filed: Aug. 31, 1998

[51] Int. Cl.[7] ..... A01H 5/00

[52] U.S. Cl. ..... Plt./356

[58] Field of Search ..... Plt./356

[56] References Cited

U.S. PATENT DOCUMENTS

P.P. 8,889 9/1994 Danziger ..... Plt./356

OTHER PUBLICATIONS

UPOV–ROM GTITM Computer Database 1999/02 GTI JOUVE Retrieval Software, Citation for 'Magic Star', Mar. 1999.

*Primary Examiner*—Howard J. Locker
*Assistant Examiner*—Wendy Anne Baker
*Attorney, Agent, or Firm*—Birch, Stewart, Kolasch & Birch, LLP

[57] ABSTRACT

The present invention relates to a new and distinct horticultural variety of petunia. This petunia denominated 'Magic Star' is a variety selected and bred from self-fertilized seeds of MS-01, possessed by the applicant. This petunia has excellent cold resistance and resistance to rain and bears bright red purple large flowers with yellowish white margins.

1 Drawing Sheet

BACKGROUND OF THE INVENTION

Petunias flower for a long time and will flower one after another from spring through autumn, thus resulting in being widely cultivated as an ornamental flower in flowerbeds, flowerpots etc.

There are a considerably large number of varieties of petunias having flowers of diverse forms. Petunia flowers range from those with a single color to those having patterns of various shapes with a different color from the background color. Generally, petunia varieties having flowers with such patterns are more popular than varieties having single-color flowers. In particular, varieties having flowers with marginal patterns have high market value.

However, petunias favor a relatively mild climate and tend to be sensitive to the photoperiod. As a result, there are instances where the plants do not fully flower when daylight hours are short due to a long rain in the summer. As such, there is a need to develop a petunia variety which is excellent in cold resistance and resistance to rain.

The present invention meets this need and the object of the present invention is to provide a novel variety of petunia (*Petunia hybrida*) which is excellent in cold resistance and resistance to rain and which has beautiful flowers with margins.

Breeding of 'Magic Star' was conducted from 1996 to 1997 in Oaza-Idei, Oyama, Tochigi, Japan and Norwich Road, Foxley, Dereham, Norfolk NR20 4SS, United Kingdom, as follows:

A seedling designated MS-01 (unpatented) possessed by the present applicant was self-pollinated in Apr. 1996, and self-fertilized seeds were obtained in May 1996 in a greenhouse of Japan Tobacco Inc., located in Oaza-Idei, Oyama, Tochigi, Japan. MS-01 bears vivid reddish purple (ISCC-NBS) (Japanese Horticultural Standard color chart number (J.H.S.) 9207, Royal Horticultural Society Colour Chart number (R.H.S.) 72B) flowers having yellowish white (J.H.S. 3301, or between R.H.S. 155B and 158C) marginal patterns.

The self-pollinated seeds were sown in August 1996 and cultivated in a greenhouse located at Norwich Road, Foxley, Dereham, Norfolk NR20 4SS, United Kingdom, and as a result, they flowered in December 1996.

The selected plant was excellent in plant information with a number of large flowers having yellowish white margins distinct from the background color of bright red purple. The selected plant was multiplied via vegetative reproduction using cuttings of the selected plant from January 1997 in a greenhouse. After multiplied plants were temporarily planted in March 1997 in pots in a greenhouse, they were transplanted to the open field in April 1997 in Norwich Road, Foxley, Dereham, Norfolk NR20 4SS, United Kingdom.

The characteristics of 'Magic Star', including the heat, rain, cold and pest resistance, were examined in the open field in June 1997, and the homogeneity and stability were confirmed thereby completing the breeding.

SUMMARY OF THE INVENTION

This petunia is characterized by having excellent cold resistance and resistance to rain and by bearing beautiful flowers with margins.

BOTANICAL DESCRIPTION

Figure 1:
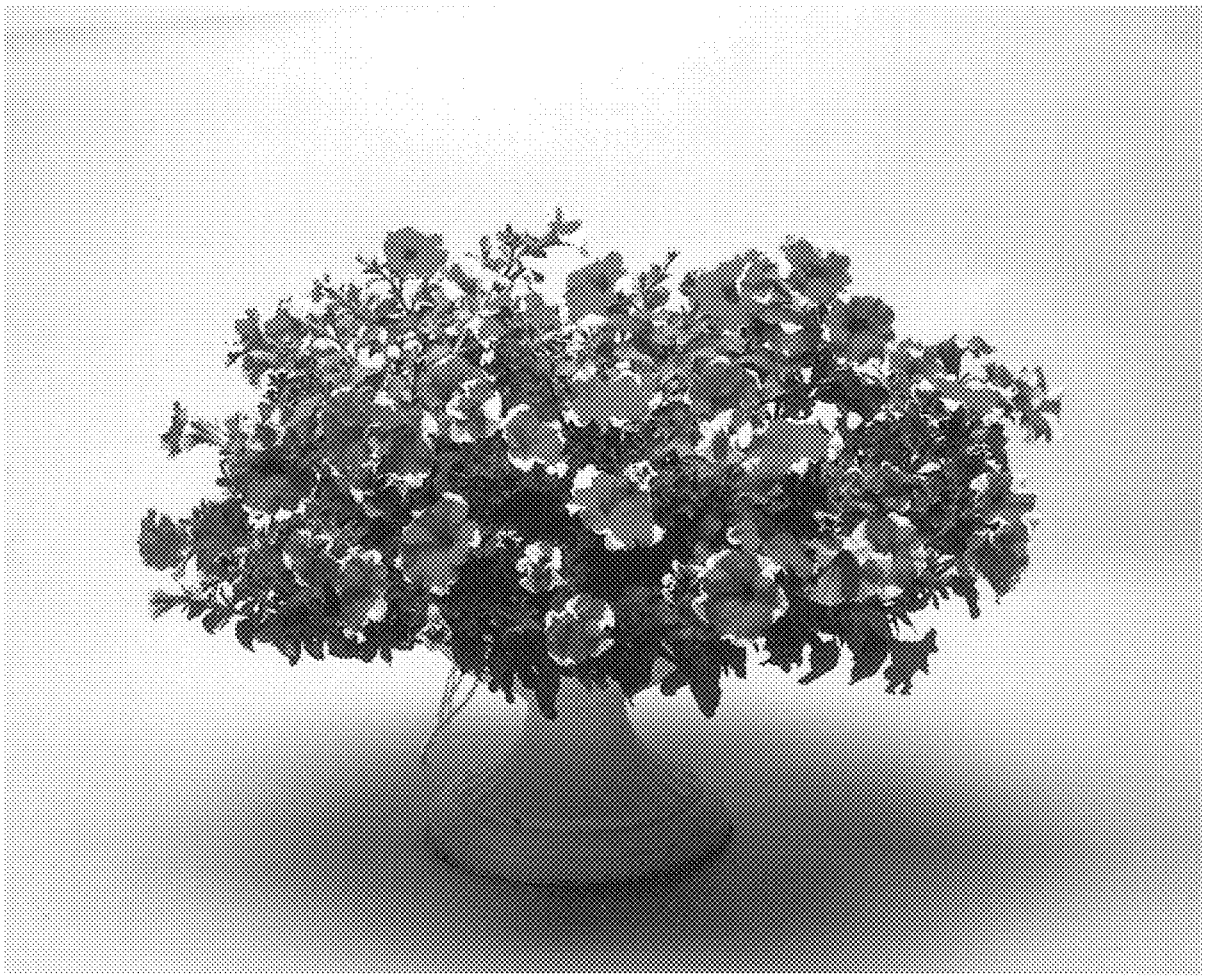
FIG. 1 is a photograph showing the whole of the present petunia plant.

The growth type is spreading, and the height is medium (20 to 30 cm). The number of primary branches is high, but the number of secondary branches is medium.

The thickness of the stem is medium (3 to 4 mm), and the quantity of the pubescence on the stem is also medium. The stem is moderate yellow green in color (J.H.S. 3712 or 3513, R.H.S. 137D). The length of the internode is short (1 to 2 cm), and the color of the leaf ranges from yellowish green to green. The shape of the leaf is lanceolate and the leaf is borne horizontally. The length of the leaf is medium (8 to 9 cm), and the width of the leaf is also medium (3 to 4.5 cm). The branch length is 20 to 30 cm. Leaves are held alternately in the juvenile growth phase, but switch to opposite phyllotaxy in the reproductive growth phase. The present petunia has no leaf pubescence.

The color of the upper and lower surfaces of the foliage ranges from moderate yellow green to dark olive green (J.H.S. 3707, 3712, or 3513, R.H.S. 137D).

The present petunia has no readily visible veins.

The flower is a single-petaled large flower of 8 to 9.5 cm in diameter, and the color of the flower is vivid reddish purple (J.H.S. 9206, R.H.S. 74A), with yellowish white margins (J.H.S. 3301, or between R.H.S. 155B and 158C). The color of the flower throat is a dark purple (J.H.S. 8609, R.H.S. 83A) stripe on a pale purple pink (J.H.S. 8902, R.H.S. 76D) background. The color of the outer side of the petals is yellowish white (J.H.S. 3301, or between R.H.S. cc 155B and 158C). The color of the underside of the petals is light purple (J.H.S. 8603, R.H.S. 84B). The flower buds are a moderate reddish purple (J.H.S. 8913, R.H.C. 79D). The width of the margin coloration ranges from 1 to 30 mm depending on feeding and cultural control. The margin width increases when nutrient levels are low. The lobation of the petal is medium and the waviness thereof is also medium. The relative position of the pistil and stamens is either "even" (that is, the pistil is as tall as the stamens) or "concave" (that is, the pistil is shorter than the stamens). The color of the pistil is vivid yellow green (J.H.S. 3705, R.H.S. 143B). The flowers have 1 pistil and 5 stamen. The flowers have 5 anthers having an elliptical shape and a dark greenish yellow color (J.H.S. 9212, R.H.S. 152C). The length and width of the peduncle are respectively 15–20 mm and about 2 mm. The shape of the calyx is typical of petunia and the calyx is medium in size. The corollas of the flowers are not entirely joined and there are lobations in the joints. The edge of the corollas weakly wave. The flowers open slanting upward in relation to the foliage and have an overall upward slant. The flowers have little fragrance.

The flowering period is classified as being medium to being late. Flowering time of the present petunia is from the beginning of May to the beginning of November in the United Kingdom. The flowers open at the beginning of May if a cutting made at the beginning of February is temporarily planted in a pot in March and then planted in a field in the U.K. at the beginning of April. The flowers open ten weeks after the cutting if the plant is grown indoors under appropriate conditions. The present petunia grows more slowly than 'Surfinia Purple' (unpatented) and its flowering time is about 10 days behind that of 'Surfinia Purple'. The number of blooms of the present petunia is about from 60 to 70 per plant.

Cold resistance, heat resistance, resistance to rain and resistance to disease are strong. Heat, rain and pest resistance are the same as that of the petunia variety 'Surfinia Purple'. Cold resistance is stronger than that of 'Surfinia Purple'. The present petunia continues to flower until the beginning of November while 'Surfinia Purple', which is a general petunia variety stops flowering towards the end of October.

Although the present petunia is similar to a petunia variety named 'Surfinia Purple', both of them are distinguished in that 'Surfinia Purple' has flowers of a single color of bright red purple whereas the present petunia has flowers with yellowish white margins in the background color of bright red purple.

The present petunia and the parent cultivar are different in flower color. The flower color of the present petunia is vivid reddish purple (J.H.S. 9206, R.H.S. 74A), while the flower color of the parent cultivar is vivid reddish purple (J.H.S. 9207, corresponding to R.H.S. 72B).

I claim:

1. A new and distinct petunia plant named 'Magic Star' substantially shown and described herein.

* * * * *